United States Patent [19]

Kulprathipanja et al.

[11] Patent Number: 4,570,029

[45] Date of Patent: Feb. 11, 1986

[54] PROCESS FOR SEPARATING ISOPRENE

[75] Inventors: Santi Kulprathipanja, Hoffman Estates; Chin-Hsiung Chang, Palatine, both of Ill.

[73] Assignee: UOP Inc., Des Plaines, Ill.

[21] Appl. No.: 707,998

[22] Filed: Mar. 4, 1985

[51] Int. Cl.$^4$ .............................................. C07C 7/12
[52] U.S. Cl. .................... 585/829; 585/826
[58] Field of Search ................................ 585/829, 826

[56] References Cited

U.S. PATENT DOCUMENTS

| | | | |
|---|---|---|---|
| B 426,274 | 1/1976 | Hedge | 260/674 SA |
| 2,985,589 | 5/1961 | Broughton et al. | 210/34 |
| 3,201,491 | 8/1965 | Stine et al. | 260/676 |
| 3,265,750 | 8/1966 | Peck et al. | 260/666 |
| 3,311,671 | 3/1967 | Baker | 260/677 |
| 3,510,423 | 5/1970 | Neuzil et al. | 208/310 |
| 3,596,436 | 8/1971 | Dassesse | 55/19 |
| 3,626,020 | 12/1971 | Neuzil | 260/674 SA |
| 3,663,638 | 5/1972 | Neuzil | 260/674 SA |
| 3,665,046 | 5/1972 | De Rosset | 260/674 SA |
| 3,668,266 | 6/1972 | Chen et al. | 260/674 |
| 3,686,343 | 8/1972 | Bearden, Jr. et al. | 260/674 SA |
| 3,700,744 | 10/1972 | Berger et al. | 260/668 A |
| 3,734,974 | 5/1973 | Neuzil | 260/674 SA |
| 3,851,010 | 11/1974 | Rescalli et al. | 260/681.5 |
| 3,894,109 | 7/1975 | Rosback | 260/674 SA |
| 3,947,506 | 3/1976 | Iybarger | 260/681.5 |
| 3,992,471 | 11/1976 | Priegnitz | 260/681.5 R |
| 3,997,620 | 12/1976 | Neuzil | 260/674 SA |
| 4,392,004 | 7/1983 | D'Sidocky | 585/829 |

FOREIGN PATENT DOCUMENTS

| | | | |
|---|---|---|---|
| 2535818 | 1/1976 | Fed. Rep. of Germany | 585/829 |
| 831357 | 3/1960 | United Kingdom | 585/829 |

Primary Examiner—Curtis R. Davis
Attorney, Agent, or Firm—Thomas K. McBride; William H. Page, II; John G. Tolomei

[57] ABSTRACT

A process for separating isoprene from isobutylene, isopentane, and pentene-1. The process uses an adsorbent comprising activated carbon or molecular sieve carbon to selectively adsorb isoprene from the other hydrocarbons. High purity isoprene is recovered by desorption using desorbent materials which include olefinic hydrocarbons. The process is particularly suited for a simulated moving bed apparatus.

7 Claims, 1 Drawing Figure

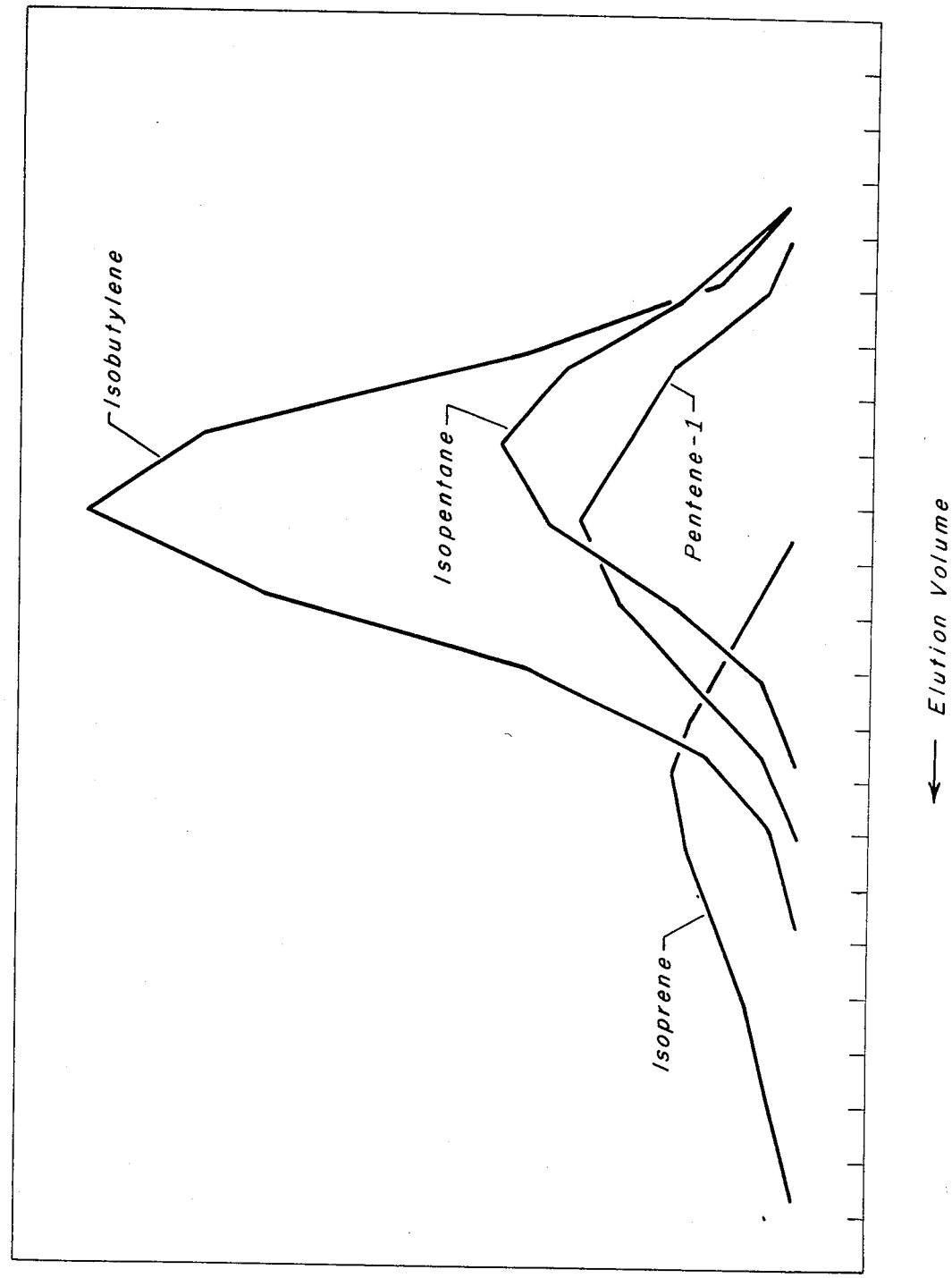

the feed with an adsorbent comprising activated carbon or molecular sieve carbon which selectively adsorbs isoprene. The feed is then removed from the adsorbent, and the isoprene is recovered by desorption at desorption conditions with a desorbent material comprising a hydrocarbon. The feed mixture and the desorbent material have boiling points of at least 5° C. difference.

PROCESS FOR SEPARATING ISOPRENE

BACKGROUND OF THE INVENTION

1. Field of the Invention

The field of art to which this invention pertains is the solid bed adsorptive separation of hydrocarbons. More specifically, the invention relates to a process for separating isoprene from a feed mixture of isoprene and at least one additional $C_4$ or $C_5$ hydrocarbon, which process employs a particular adsorbent to selectively adsorb isoprene from the feed mixture.

2. Background Information

The use of crystalline aluminosilicates to perform hydrocarbon separation is well known in the separation art. Examples of such separations are disclosed in U.S. Pat. Nos. 2,985,589 and 3,201,491 wherein a type A zeolite is used to separate normal paraffins from branched chain paraffins. The use of faujasites to separate olefinic hydrocarbons from paraffinic hydrocarbons is described in U.S. Pat. Nos. 3,265,750 and 3,510,423. These adsorbents allow a separation based on the physical size differences in the molecules by allowing the smaller or normal hydrocarbons to be passed into the cavities within the zeolitic adsorbent, while excluding the larger or branched chain molecules.

In addition to being used in processes for separating hydrocarbon types, adsorbents comprising type X or Y zeolites have also been employed in processes to separate individual hydrocarbon isomers. In the processes described, for example, in U.S. Pat. Nos. 3,626,020 to Neuzil, 3,663,638 to Neuzil, 3,665,046 to deRosset, 3,668,266 to Chen et al., 3,686,343 to Bearden Jr. et al., 3,700,744 to Berger et al., 3,734,974 to Neuzil, 3,894,109 to Rosback, 3,997,620 to Neuzil and B426,274 to Hedge, particular zeolitic adsorbents are used to separate the para isomer of bialkyl substituted monocyclic aromatics from the other isomers, particularly para-xylene from other xylene isomers.

Other adsorptive separation art deals specifically with the separation of 1,3-butadiene from other $C_4$ hydrocarbons, particularly monoolefins. U.S. Pat. Nos. 3,311,671 to Baker and 3,992,471 to Priegnitz teach the use of alkali metal-aluminum silicates on zeolites in effecting that separation. U.S. Pat. No. 3,596,436 to Dassesse discloses the use of activated charcoal to separate diolefins from monoolefins, but requires that the entire process be carried out in the vapor phase and provides for the regeneration of the solid adsorbent (removal of diolefins) with superheated steam. There is also separation art dealing specifically with the separation of isoprene from $C_5$ hydrocarbon streams utilizing such methods as distillation, extractive distillation, liquid-liquid extraction and chemical treatment. Typical of such procedures is that shown in U.S. Pat. No. 3,851,010 and 3,947,506 which use distillations and extraction to recover high purity isoprene.

In contradistinction to the prior art, the present invention achieves the separation of isoprene from specific $C_4$ and $C_5$ hydrocarbons using an activated carbon or molecular sieve carbon adsorbent.

SUMMARY OF THE INVENTION

In brief summary the invention is, in one embodiment, a process for separating isoprene from a feed mixture comprising isoprene and at least one other hydrocarbon from the group consisting of isobutylene, isopentane and pentene-1. The process comprises contacting in liquid phase at adsorption conditions, the feed with an adsorbent comprising activated carbon or molecular sieve carbon which selectively adsorbs isoprene. The feed is then removed from the adsorbent, and the isoprene is recovered by desorption at desorption conditions with a desorbent material comprising a hydrocarbon. The feed mixture and the desorbent material have boiling points of at least 5° C. difference.

Other embodiments of the present invention encompass details about feed mixtures, desorbents, flow schemes and operating conditions, all of which are hereinafter disclosed in the following discussion of each of the facets of the present invention.

DESCRIPTION OF THE INVENTION

At the outset the definitions of various terms used throughout this specification will be useful in making clear the operation, objects and advantages of the present invention.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound that is more selectively adsorbed by the adsorbent while a "raffinate component" is a compound or type of compound that is less selectively adsorbed. In this process, isoprene is the extract component and one or more other $C_4$ and $C_5$ hydrocarbons is a raffinate component. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely nonadsorbed by the adsorbent. Therefore, small amounts of a raffinate component can appear in the extract stream and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed isoprene to the concentration of less selectively adsorbed other $C_4$-$C_5$ hydrocarbons will be highest in the extract stream, next highest in the feed mixture, and lowest in the raffinate stream. Likewise, the ratio of the less selectively adsorbed other $C_4$-$C_5$ hydrocarbons to the more selectively adsorbed isoprene will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operations to take place for a given quantity of adsorbent.

Isoprene is a favorite building block in nature and occurs in many compounds which can be derived from plant and animal compounds; however, its primary commercial value lies in the rubber industry. Natural rubber could be considered a polymer of isoprene. Interest in synthetic cis-polyisoprene and the isoprene monomer has increased recently due to predictions that the demand for natural rubber will exceed supply before the end of the century and upward fluctuations in the cash price for natural rubber.

Principal commercial sources for isoprene are extraction or distillation of isoprene from $C_5$ hydrocarbon streams; reaction of isobutene with formaldehyde; dehydrogenation of tertiary amylene isomers; and the reaction, hydrogenation, and hydration of acetone and acetylene. Other sources of isoprene include conversion processes using propylene, isopentane, butenes, or isopentene as starting components.

All of the conversion processes for isoprene yield a product which also contains other closely boiling hydrocarbons. Therefore the conversion processes are similar to the extraction or distillation processes in that each ultimately demands the removal of hydrocarbons or contaminants to yield a high purity isoprene product. Isolation and purification of isoprene to polymerization grade quality is important due to its principal use in the production of cis-polyisoprene by a stereospecific polymerization procedure. Thus the presence of impurities pose significant problems due to the sensitivity of such procedures to contamination.

This invention simplifies purification procedures by providing a simple and effective method of removing isoprene from certain $C_4$ and $C_5$ hydrocarbons. Thus it was discovered that certain adsorbents will adsorb isoprene to substantial exclusion of isobutylene, isopentane and pentene-1. Accordingly an appropriate feed mixture for practicing this invention comprises isoprene and isobutylene, isopentane and pentene-1 whether alone or in combination. However, it is impractical to obtain feed mixtures completely free of other $C_4$ or $C_5$ hydrocarbons, thus suitable feed mixtures can also contain minor portions of other similar boiling point hydrocarbons which may be removed with either the extract or raffinate. Typical sources for the feed mixture of this invention are $C_5$ cracking fractions from naphtha or gas oils and dehydrogenation products from isopentane and isopentenes.

To separate the isoprene from a feed mixture in accordance with the present invention, the mixture is contacted with the adsorbent and the isoprene is more selectively adsorbed and retained by the adsorbent while the other components of the feed mixture are relatively unadsorbed and are removed from the interstitial void spaces between the particles of adsorbent and the surface of the adsorbent. The adsorbent containing the more selectively adsorbed isoprene is referred to as a "rich" adsorbent. The isoprene is then recovered from the rich adsorbent by contacting the rich adsorbent with a desorbent material.

The term "desorbent material" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is therefore contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. In the preferred isothermal, isobaric, liquid-phase operation of the process of this invention, it has been found that the effective desorbent materials comprise hydrocarbons, particularly olefinic hydrocarbons having more than five carbon atoms.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possesses adsorptive selectivity, (B) for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material, or in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A fourth important property of the adsorbent is the absence of reactivity or catalytic function that would cause undesirable chemical changes to the feed and desorbent components. The above U.S. Patents to Baker and Priegnitz, for example, teach the use of zeolitic materials as adsorbents. Such materials, however, are known to react with hydrocarbons, particularly olefins. In contradistinction to such chemically active adsorbents, the carbon adsorbents of the present invention are chemically inert to the components of the process streams.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer and the particular $C_4$ and $C_5$ hydrocarbons all diluted in desorbent is injected for a duration of several minutes. Desorbent flow is resumed, and the tracer and the feed isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one hydrocarbon with respect to another, and the rate of desorption of an extract component by the desorbent. The capacity index may be characterized by the distance between the center of the peak envelope of the selectively adsorbed component and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The adsorbent to be used in the process of this invention comprises what is known as activated carbon or molecular sieve carbon. Activated carbon is a common, commercially available material, such as Calgon Corporation's "Type PCB" granular carbon, or Union Carbide Corporation's material having the trademark "PURASIV". Type PCB as described in Calgon's brochure No. 23-108a, dated August 1978, incorporated herein by reference, is an activated carbon having a large micropore volume, the range of 15 to 20 Angstrom units in diameter, permeated by a system of macropores larger than 1000 Angstroms in diameter. PURASIV, as described in Union Carbide's brochure F-4866815M, incorporated herein by reference, is a beaded activated carbon made from molten petroleum pitch shaped into spherical particles and subsequently carbonized and activated.

The term "molecular sieve carbon" as used herein is not intended to necessarily distinguish from those materials referred to as "activated carbon" but to ensure that no material effective for use in the present invention is excluded. There is considerable overlap between the two terms in question and probably in most instances, for purposes of the present invention, the terms are interchangeable. The particular molecular sieve carbons known to be effective for use in the present invention are those having an average pore size in excess of about 5 Angstrom units.

The adsorbent may be in the form of particles such as extrudates, aggregates, tablets, macrospheres or granules having a desired particle range, preferably from about 16 to about 60 mesh (Standard U.S. Mesh). Less water content in the adsorbent is advantageous from the standpoint of less water contamination of the product.

The adsorbent may be employed in the form of a dense fixed bed which is alternatively contacted with a feed mixture and a desorbent material in which case the process will be only semi-continuous. In another embodiment, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the co-current high efficiency simulated moving bed process disclosed in U.S. Pat. No. 4,402,832 to Gerhold, incorporated by reference herein in its entirety.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is preferred for this process because of the lower temperature and energy requirements and because of the higher yields of an extract product that can be obtained with liquid-phase operation over those obtained with vapor-phase operation. Adsorption conditions will include a temperature range of from about 20° C. to about 250° C., with about 50° C. to about 200° C. being more preferred, and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

The following example is presented for illustration purposes and more specifically is presented to illustrate the selectivity relationships that make the process of the invention possible. Reference to specific desorbent materials, feed mixtures and operating conditions is not intended to unduly restrict or limit the claims of this invention.

EXAMPLE

In this experiment, a pulse test was performed to evaluate the ability of the present invention to separate isoprene from isobutylene, isopentane, and pentene-1 using a carbon adsorbent.

The testing apparatus was the above described pulse test apparatus. For the pulse test, the column was maintained at a temperature of 65° C. and a pressure sufficient to maintain liquid-phase operations. Gas chromatographic analysis equipment was attached to the column effluent stream in order to determine the composition of the effluent material at given time intervals. The feed mixture employed for the test contained about 5 vol. % each of isoprene, isopentane, isobutylene, pentene-1 and 80 vol. % desorbent material. The desorbent material was hexene-1. The operations taking place for the test were as follows. The desorbent material was run continuously at a nominal liquid hourly space velocity (LHSV) of 1.0 which amounted to about 1.17 cc per minute feed rate of desorbent. At some convenient time interval the desorbent was stopped and the feed mixture was run for a 10 minute interval at a rate of 1.0 cc per minute. The desorbent stream was then resumed at 1 LHSV and continued to pass into the adsorbent column until all of the feed components had been eluted from the column as determined by observing the chromatograph generated by the effluent material leaving the adsorption column. The sequence of operations usually takes about an hour. The 10 minute pulse of feed and subsequent desorption may be repeated in sequence as often as is desired. The chromatograph tracing obtained is shown in the attached figure. Retention volume and adsorption rate data derived from the trace are given below, the reference curve being isopentane which is presumed to be totally non-adsorbed.

| Component | Retention Volume | Peak Half Width |
|---|---|---|
| Isobutylene | 3 | 12.6 |
| Isopentane | 0 | 12.7 |
| Pentene-1 | 2.6 | 15.2 |
| Isoprene | 16.0 | 15.8 |

The tracing of the figure for the test shows a clear and distinct separation of isoprene from the other feed components. The isoprene is the last component to elute from the pulse test which is indicative of being the most selectively retained component on the carbon adsorbent. In addition, high selectivities of 5.3 and 6.2 relative to the respective separation of isoprene/isobutylene and isoprene/pentene-1 were calculated for the adsorbent. These high selectivities relative to the second and third most strongly adsorbed components is conclusive quantitative evidence of a high degree of separation.

We claim as our invention:

1. A process for separating isoprene from a feed mixture comprising isoprene and at least one additional hydrocarbon, selected from the group consisting of isobutylene, isopentane, and pentene-1 which process comprises contacting at adsorption conditions said mixture with an adsorbent comprising activated carbon or molecular sieve carbon, selectively adsorbing said isoprene to substantial exclusion of other said hydrocarbons, removing the non-adsorbed portion of the feed mixture from contact with the adsorbent, and thereafter recovering high purity isoprene by desorption at desorption conditions.

2. The process of claim 1 wherein said adsorption and desorption conditions include a temperature of from about 20° C. to about 250° C. and a pressure sufficient to maintain liquid phase.

3. The process of claim 1 wherein the desorbent material comprises an olefinic hydrocarbon having six or more carbon atoms.

4. The process of claim 1 wherein the desorbent material is hexene-1.

5. The process of claim 1 wherein said separation is effected by means of a simulated moving bed flow scheme.

6. The process of claim 5 wherein said simulated moving bed scheme uses a countercurrent flow.

7. The process of claim 5 wherein said simulated moving bed scheme uses co-current flow.

* * * * *